(12) United States Patent
Hestekin et al.

(10) Patent No.: US 10,933,184 B2
(45) Date of Patent: Mar. 2, 2021

(54) DIALYSATE FREE ARTIFICIAL KIDNEY DEVICE

(71) Applicant: US Kidney Research Corporation, Roseville, CA (US)

(72) Inventors: Jamie Allen Hestekin, Fayetteville, AR (US); Christa Noel Hestekin, Fayetteville, AR (US); Grace Ann C. Morrison, Springdale, AR (US); Sadia Ali Paracha, Fayetteville, AR (US)

(73) Assignee: US Kidney Research Corporation, Roseville, CA (US)

( * ) Notice: Subject to any disclaimer, the term of this patent is extended or adjusted under 35 U.S.C. 154(b) by 611 days.

(21) Appl. No.: 15/732,169

(22) Filed: Sep. 27, 2017

(65) Prior Publication Data

US 2018/0093030 A1   Apr. 5, 2018

Related U.S. Application Data

(60) Provisional application No. 62/495,981, filed on Sep. 30, 2016.

(51) Int. Cl.
*B01D 61/44* (2006.01)
*A61M 1/16* (2006.01)
(Continued)

(52) U.S. Cl.
CPC ........ *A61M 1/1696* (2013.01); *A61M 1/1006* (2014.02); *A61M 1/1605* (2014.02);
(Continued)

(58) Field of Classification Search
CPC .............. A61M 1/1006; A61M 1/1678; A61M 1/3482; A61M 1/1654; A61M 1/1696;
(Continued)

(56) References Cited

U.S. PATENT DOCUMENTS 5,026,465 A * 6/1991 Katz ...................... B01D 61/48
204/524
5,858,191 A   1/1999 DiMascio et al.
(Continued)

FOREIGN PATENT DOCUMENTS

CN        1843956      10/2006
CN     101862481 A    10/2010
(Continued)

OTHER PUBLICATIONS

Ho, T. et al. (Feb. 25, 2010). "Wafer Chemistry and Properties for Ion Removal by Wafer Enhanced Electrodeionization," *Separation Science and Technology* 45(4):433-446.
(Continued)

*Primary Examiner* — Cameron J Allen
(74) *Attorney, Agent, or Firm* — Morrison & Foerster LLP

(57) ABSTRACT

A device and method are described for the treatment of blood, which device may be used in conjunction with or in place of a failed Kidney. The device includes an ultrafiltration unit to remove proteins, red and white blood cells and other high molecular weight components, a nanofiltration unit to remove glucose, at least one electrodeionization unit to transport ions from the blood stream, and a reverse osmosis unit to modulate the flow of water, to both the blood and urine streams. In one embodiment, a specialized electrodeionization unit is provided having multiple chambers defining multiple dilute fluid channels, each channel filled with an ion specific resin wafer, and electrodes at the extremity of the device and proximate each of the resin filled dilute channels. By selective application of voltages to these electrodes, the ion transport functionality of a given dilute channel can be turned on or off.

20 Claims, 9 Drawing Sheets

(51) Int. Cl.

| | |
|---|---|
| *A61M 1/10* | (2006.01) |
| *A61N 1/00* | (2006.01) |
| *A61M 1/34* | (2006.01) |
| *B01D 61/50* | (2006.01) |
| *B01D 61/58* | (2006.01) |
| *B01D 61/02* | (2006.01) |
| *B01D 61/32* | (2006.01) |
| *B01D 61/48* | (2006.01) |
| *C02F 9/00* | (2006.01) |
| *B01D 61/54* | (2006.01) |
| *B01D 61/12* | (2006.01) |
| *B01D 61/14* | (2006.01) |
| *B01D 61/28* | (2006.01) |
| *B01D 61/24* | (2006.01) |
| *A61M 1/28* | (2006.01) |
| *A61M 1/36* | (2006.01) |
| *A61M 1/12* | (2006.01) |
| *C02F 1/44* | (2006.01) |
| *C02F 1/469* | (2006.01) |

(52) U.S. Cl.
CPC ........ *A61M 1/1654* (2013.01); *A61M 1/1678* (2013.01); *A61M 1/3472* (2013.01); *A61M 1/3482* (2014.02); *A61N 1/00* (2013.01); *B01D 61/022* (2013.01); *B01D 61/12* (2013.01); *B01D 61/145* (2013.01); *B01D 61/246* (2013.01); *B01D 61/28* (2013.01); *B01D 61/32* (2013.01); *B01D 61/44* (2013.01); *B01D 61/445* (2013.01); *B01D 61/48* (2013.01); *B01D 61/485* (2013.01); *B01D 61/50* (2013.01); *B01D 61/54* (2013.01); *B01D 61/58* (2013.01); *C02F 9/00* (2013.01); *A61M 1/12* (2013.01); *A61M 1/165* (2014.02); *A61M 1/1649* (2014.02); *A61M 1/28* (2013.01); *A61M 1/3639* (2013.01); *A61M 2205/3331* (2013.01); *A61M 2209/088* (2013.01); *B01D 2311/243* (2013.01); *B01D 2311/2684* (2013.01); *B01D 2313/40* (2013.01); *B01D 2317/02* (2013.01); *B01D 2325/42* (2013.01); *C02F 1/441* (2013.01); *C02F 1/442* (2013.01); *C02F 1/444* (2013.01); *C02F 1/4695* (2013.01)

(58) Field of Classification Search
CPC .... A61M 1/1605; A61M 1/3472; A61M 1/28; A61M 2205/3331; A61M 1/165; A61M 1/3639; A61M 1/12; A61M 1/1649; A61M 2209/088; B01D 61/44; B01D 61/145; B01D 61/28; B01D 61/485; B01D 61/022; B01D 61/445; B01D 61/12; B01D 61/246; B01D 61/48; B01D 61/32; B01D 61/54; B01D 61/50; B01D 61/58; B01D 2311/2684; B01D 2317/02; B01D 2311/243; B01D 2325/42; B01D 2313/40; C02F 9/00; C02F 1/441; C02F 1/442; C02F 1/444; C02F 1/4695; A61N 1/00

See application file for complete search history.

(56) References Cited

U.S. PATENT DOCUMENTS

| | | |
|---|---|---|
| 6,284,124 B1 | 9/2001 | DiMascio |
| 6,905,608 B2 | 6/2005 | Reinhard |
| 7,141,154 B2* | 11/2006 | Lin ................... B01D 61/48 204/524 |
| 7,501,064 B2 | 3/2009 | Schmidt et al. |
| 8,585,882 B2 | 11/2013 | Freydina |
| 8,764,981 B2 | 7/2014 | Ding et al. |
| 8,858,792 B2 | 10/2014 | Ding et al. |
| 9,005,440 B2 | 4/2015 | Lin et al. |
| 2004/0245175 A1 | 12/2004 | Godec et al. |
| 2006/0231403 A1 | 10/2006 | Rivello |
| 2011/0198286 A1* | 8/2011 | Niazi ................ C12M 23/14 210/638 |
| 2012/0289881 A1 | 11/2012 | Lyn et al. |

FOREIGN PATENT DOCUMENTS

| | | |
|---|---|---|
| JP | H07-328395 A | 12/1995 |
| JP | 2009-142724 A | 7/2009 |

OTHER PUBLICATIONS

Pan, S.-Y. et al. (Mar. 2, 2017). "Development of a Resin Wafer Electrodeionization Process for Impaired Water Desalination with High Energy Efficiency and Productivity," *ACS Sustainable Chemistry & Engineering* 5(4):2942-2948.

International Search Report and Written Opinion of the International Searching Authority dated Aug. 6, 2018 for PCT Application No. PCT/US2018/000004 filed on Jan. 26, 2018, 26 pages.

Invitation to Pay Additional Fees and, Where Applicable, Protest Fee dated Jun. 14, 2018 for PCT Application No. PCT/US2018/000004 filed on Jan. 26, 2018, 18 pages.

Fissell et al. Achieving more Freq.and Longer Dialysis for the Majority: Weareable Dialysis and Impl. Artificial Kideny Devices. Kindney International (2013), 84 256-264.

* cited by examiner

| EDI Wafer | Resin Composition of Wafer | Na | K | Ca | Cl | Mg |
|---|---|---|---|---|---|---|
| 1 | Amberlite (50% IR120, 50% IRA-400) | 1.00 | 1.65 | 1.94 | 1.04 | 1.65 |
| 2 | Amberlite (75% IR120, 25% IRA-400) | 1.00 | 2.39 | 2.62 | 1.33 | 1.47 |
| 3 | Amberlite (25% IR120, 75% IRA-400) | 1.00 | 1.17 | 1.60 | 1.00 | 0.00 |
| 4 | Amberlite (50% IR120, 50% IRA-900) | 1.00 | 1.61 | 23.01 | 13.5 | 14.61 |
| 5 | Amberlite (25% IRP-69, 75% IRA-400) | 1.00 | 1.89 | 2.17 | 1.25 | 1.18 |
| 6 | 50% DOWex MAc3, 50% Amberlite IRA0400 | 1.00 | 3.96 | 5.12 | 2.73 | 3.25 |
| 7 | Amberlite (50% IR120, 50% FPA55) | 1.00 | 2.60 | 3.77 | 1.55 | 1.32 |
| 8 | Amberlite (50% IR120, 50% IRN-78) | 1.00 | NA | 1.44 | 0.84 | 0.78 |
| 9 | Amberlite (50% IR120, 50% IRA-402) | 1.00 | 5.31 | 5.85 | 3.01 | 9.37 |
| 10 | Amberlite (50% IRN-77, 50% IRA-402) | 1.00 | 1.38 | 1.58 | 1.08 | 1.99 |
| 11 | Amberlite (50% IRN-77, 50% IRA-78) | 1.00 | 0.68 | 0.96 | 0.46 | -10.25 |

*ion transport rates are normalized to sodium transport

Table 1

FIG. 7A

| Wafer | Resin Composition of Wafer | Na | K | Ca | Cl | Mg |
|---|---|---|---|---|---|---|
| 1 | Amberlite (50% IR120, 50% IRA-400) | 2572.15 | 177.00 | 55.51 | 92.74 | 8.27 |
| 2 | Amberlite (75% IR120, 25% IRA-400) | 781.25 | 100.00 | 82.98 | 37.17 | 3.51 |
| 3 | Amberlite (25% IR120, 75% IRA-400) | 1773.44 | 100.00 | 104.37 | 40.83 | 4.43 |
| 4 | Amberlite (50% IR120, 50% IRA-900) | 122.50 | 8.62 | 126.04 | 113.40 | 2.49 |
| 5 | Amberlite (25% IRP-69, 75% IRA-400) | 968.75 | 83.57 | 70.32 | 60.41 | 1.85 |
| 6 | 50% DOWex MAc3, 50% Amberlite IRA0400 | 508.07 | 130.93 | 99.29 | 73.25 | 2.41 |
| 7 | Amberlite (50% IR120, 50% FPA55) | 112.79 | 103.70 | 114.71 | 54.45 | 0.84 |
| 8 | Amberlite (50% IR120, 50% IRN-78) | 1810.60 | NA | 97.96 | 120.59 | 1.45 |
| 9 | Amberlite (50% IR120, 50% IRA-402) | 290.32 | 85.00 | 70.16 | 44.81 | 1.67 |
| 10 | Amberlite (50% IRN-77, 50% IRA-402) | 1301.59 | 74.86 | 82.53 | 101.10 | -0.10 |
| 11 | Amberlite (50% IRN-77, 50% IRA-78) | 1785.72 | 73.71 | 102.03 | 51.03 | 0.18 |

* Concentrations are in ppm

Table 2

FIG. 7B

DIALYSATE FREE ARTIFICIAL KIDNEY DEVICE

BACKGROUND OF THE INVENTION

Field of the Invention

This invention relates generally to a device for removing ions from a fluid stream, and more particularly a device for the treatment of blood. More particularly, it relates to a separation device and method for the removal of certain ions and organic molecules from the blood, as well as a multi-component device for effecting such removal. In one particular, it relates to a specialized electrodeionization unit capable of selectively removing ions from the blood stream. In another particular, it relates to a portable, wearable, or partially or wholly implantable device for the treatment of human blood incorporating the specialized electrodeionization unit of the invention, which device may be used along with or in place of a human kidney to remove toxins without the use of a dialysate.

DESCRIPTION OF THE RELATED ART

The kidneys are responsible for a number of key functions required to keep one alive. In general, the kidneys keep both the content and blood concentration of water, several ions, and various organic compounds constant from day to day despite constant changes in dietary intake of these substances. The kidneys accomplish this by regulating the amount of water, ions and organics they excrete to match the changes in the amount of water, ions, and organics absorbed by the gastrointestinal tract from liquids and solid foods in a diet.

The term "function of the kidneys" is a misnomer since the kidney has several different functions. Specifically, the kidneys control the amount of water and salt in our bodies and therefore the amount of fluid in blood vessels. This function is an important determinant of blood pressure and therefore the kidneys play a key role in blood pressure control. The kidneys also regulate the chemistry of blood by controlling the blood concentration of potassium, sodium, chloride, bicarbonate, calcium, magnesium, and phosphorus. The kidneys are responsible for maintaining whole body nitrogen balance by excreting dietary nitrogen intake in the form of urea. The kidneys also make two important hormones: erythropoietin, which stimulates bone marrow to make red blood cells and the active form of vitamin D, which maintains bone health.

Chronic kidney disease (CKD) and ultimately End Stage Renal Disease (ESRD) refer to a global loss of kidney function. Patients transition through a series of CKD stages (I-V) that refer to a worsening loss of global function until they reach ESRD at which point renal replacement therapy is required in the form of dialysis (hemodialysis or peritoneal dialysis) or kidney transplant.

In addition to the global loss of function in CKD/ESRD patients, other kidney diseases can separately affect each of the kidney's specific functions. For example, there are disorders that affect the ability of the kidney to excrete potassium; disorders that affect renal calcium excretion; and disorders that affect renal water excretion. The current treatment for these disorders is typically pharmacologic (if available).

Various approaches for the removal of these ions and organic molecules are in use today in the acute setting and in patients who require chronic renal replacement therapy. In an outpatient setting for patients with ESRD, hemodialysis, and peritoneal dialysis are currently used modalities. Native kidney transplants are optimal. However, because of a national organ donation shortage in the United States, there are currently ~100,000 patients on the waiting list for a kidney transplant.

Chronic hemodialysis requires the placement of an AV fistula or graft, and the use of a dialysate solution that is infused into a hemodialysis cartridge during dialysis. Patients are typically dialyzed three times per week for 3-3.5 hours per session. Chronic peritoneal dialysis requires the placement of a permanent peritoneal catheter, and during this procedure, a dialysate solution is administered and then repeatedly drained from the peritoneal cavity over a 10-hour period.

One drawback with dialysis therapies is their requirement for the administration of dialysate solutions, into either the hemodialysis cartridge (hemodialysis) or the peritoneal cavity (peritoneal dialysis). Secondly, they are not continuous therapies but are intermittent therapies that provide intermittent clearance of ions and organic molecules. In hemodialysis, changes in blood pressure and other hemodynamic parameters can occur because of the acute nature of the treatment that is compressed to a 3-3.5 hour treatment period. In neither hemodialysis nor peritoneal dialysis can each of the medically relevant ions or organic molecules be specifically removed, nor with feedback control. In hemodialysis, needles are required to access the fistula or graft for each treatment, increasing the possibility of a blood infection. In peritoneal dialysis, there is a risk of peritonitis when dialysate is placed into the peritoneal cavity.

Numerous advantages over hemodialysis and peritoneal dialysis would result from being able to provide a patient the option of an artificial kidney. (1) An artificial kidney enables continuous therapy that can provide 24-hour treatment and therefore higher clearances of ions and organic molecules. (2) There is no need for a separate dialysate solution with its ensuing cost to the healthcare system. (3) There is less possibility of infection (blood infection or peritonitis) given the constant vascular hookup (central vein double lumen catheter or A-V hookup) that will result in less hospital admissions and antibiotic therapy. (4) With an artificial kidney, ions and organic molecules can be specifically transported with sensor feedback in a closed loop approach to provide regulation of the transport rate based on the patient's blood level of each substance that will change dynamically because of dietary intake, changes in GI absorption, and any residual renal function. (5) An artificial kidney will contribute to decreasing the number of patients on the waiting list for a native kidney transplant, resulting in less morbidity and mortality that typically occurs prior to a transplant. (6) For those individuals who have failed one or more native kidney transplants, the artificial kidney offers these patients another viable option that will prevent them from having to return to a dialysis modality. (7) The artificial kidney can be used when patients reach CKD stage 4 or 5 prior to having initiated dialytic therapy, thereby preventing the ensuing morbidity and mortality that is associated with hemodialysis and peritoneal dialysis therapies.

It would be ideal to have a self-contained artificial kidney, small enough to be portable, wearable externally on the body, or implantable. Such an artificial kidney would allow a patient greater mobility and flexibility and significantly improve the quality of their life than afforded by traditional dialysis. An important consideration lies in the fact the kidney not only filters blood, but also selectively transports water, various ions, and organics into the urine based on the needs of the body. For an artificial kidney to have value as a replacement for native kidney functionality, at a minimum it needs to be: 1) portable and preferably implantable, 2) not require the use of external solutions, 3) not rely on cells or enzymes which may have short lifetimes, and 4) be externally controllable.

Several solutions have been proposed in both the patent and open literature. In Fissell et al. (W H Fissell, S Roy, and A. Davenport, "Achieving more frequent and longer dialysis for the majority: wearable dialysis and implantable artificial kidney devices", Kidney International, 84 (2), 256-264 (2013)), a device is described where an ultrafiltration system is used to remove proteins and cells from the blood while renal proximal tubule cells from discarded transplant kidneys are immobilized on a construct to perform the ion transport function of the kidney.

Not addressed by Fissell is the fact the native kidney contains very many cell types, each of which have specific ion and organic molecule transport functions. The cells used by these authors do not have all the specialized transport properties of the various cell types in a native kidney. Moreover, cells grown in vitro typically change their transport properties and do not express the same proteins as they do in vivo. In addition, cells in vitro have a finite lifespan and will die or be potentially rejected and will then detach from their support. Ultimately, many different cell types with specific transport properties would be required to perform the additional functions required in to replace the transport function of the native kidney. With such a cell-based approach, no one has yet been able to simulate the numerous transport properties of the various cell types in the native kidney outside of the kidney (in vitro).

In Ding et al. (U.S. Pat. No. 8,858,792) a hemodialysis system is described wherein dialysate is regenerated using electrodeionization. This patent uses electrodeionization only for dialysate recycle. In no embodiment does it use a dialysate free system employing selective resin wafers for selective separation of ions without a dialysate. The patent does not allow for an implantable device because of the use of a dialysate, and is only controllable by changing the dialysate solution.

Dong and Wang (Chinese Patent 101,862,481A) describe a process where dialysis equipment is connected to electrodeionization and reverse osmosis devices for cleanup of the dialysate. As this process involves the use of a dialysate, it could never be implantable. Huang (Chinese Patent 1,843,956A) describe a similar process to Dong and Wang where a dialysate is required. There have been several different patents on the use of electrodeionization for various water applications but none describes using a single device to specifically control the transport of various ions from a dynamic feed stream. DiMascio et al. (U.S. Pat. No. 6,284,124) describe a device where one wafer has alternating layers of anion and cation exchange resin but there is no mention of different wafers in different compartments and there is no control of the transport of specific ions using these wafers. In DiMascio and Ganzi, U.S. Pat. No. 5,858,191, a similar process is described.

Rivello (US Published Patent Application 2006/0231403) describes a process where two ion exchange resins are used, one for anion exchange and one for cation exchange. This process, however, does not use multiple mixed resins that can selectively demineralize. Schmidt et al. (U.S. Pat. No. 7,501,064) describe a process where an electrodeionization (EDI) device is used in conjunction with a reverse osmosis device but the process is for purifying water, not for selective transport of specific ions. Furthermore, there is no description of selective wafers. Freydina and Gifford (U.S. Pat. No. 8,585,882) describe a process for using mixed media for ion depletion, absorption, adsorption, and chelation. This device describes chambers that can perform several functions. However, Freydina does not describe a system that is capable of taking one wafer offline. It does not describe in any embodiment selective deionization from a mixed feed and a controllable process for the system. Reinhard (U.S. Pat. No. 6,905,608) shows an EDI unit coupled with a filter and describes an EDI process where several different chambers specifically remove ions. However, there is no description of using this system switching current and flow to selectivity change ion selectivity as system is running.

What is evident is that none of these references provides a total solution, one that can be adopted for the cleansing of blood in an external or ultimately implantable device in patients. Despite best efforts, there remains the need for a system for the treatment of blood to remove certain ions much in the manner of an artificial kidney, which is self-contained, that can be used externally or ultimately implanted into a subject, and function autonomously, to provide a near replacement for a failed native kidney.

SUMMARY OF THE INVENTION

The present invention describes a way of using a series of interdependent separation technologies which, when incorporated into a single multi-component separation device is externally portable or implantable, and provides a treatment system capable of mimicking the operation of the native kidney. This occurs without the use of a dialysate. The artificial kidney of this invention uses different separation techniques to perform the various kidney filtration and transport functions. In the described invention an ultrafiltration device is the first unit in a process sequence where the concentrate (containing cells and proteins) is returned to the blood stream while the permeate (containing glucose, urea, creatinine, and all ions) is cycled to the next process unit.

In the next process step a nanofiltration membrane separates out glucose, the glucose retained in the concentrate sent back to the blood stream, while the permeate (containing urea, creatinine, and all ions) cycled to the next separation unit, where electrodeionization (EDI) is used to affect ion removal. In one embodiment, two selective electrodeionization units are used in sequence for ion removal. In another embodiment, the nanofiltration unit is positioned between the first and second EDI units.

The first electrodeionization unit is highly selective for the removal of potassium, sending the potassium rich concentrate to the urine stream. The second electrodeionization unit is used to remove additional ions from the blood stream (sodium, magnesium, etc.), and sends the dilute of that EDI unit to the urine stream at ratios that provide a similar composition to that of urine produced by a healthy, human kidney. For both electrodeionization units, ions that do not need to be removed via the urine are returned back to the blood stream.

After EDI processing, the urine stream is sent to a reverse osmosis unit where the appropriate amount of water is removed and returned to the blood stream to prevent dehydration. While it is important to take into account the amount of water returned to the body, the methodology for controlling the amount of water removed by the reverse osmosis unit is not addressed herein.

In summary, the invention described is a device that includes ultrafiltration to remove proteins and cells, nanofiltration to remove glucose, electrodeionization to transport ions, and reverse osmosis to modulate the flow of water, both to the blood and urine streams.

A unique aspect of this system is ability of the device to alter the magnitude of the transport of various substances to and from the blood, in order to maintain the concentration of these substances in the bloodstream relatively constant. The substances whose rate of transport are altered by the device include but are not limited to potassium, sodium, calcium, magnesium, chloride, phosphate, sulfate, bicarbonate, urea, ammonia, creatinine, and water. The ability to maintain the chemistry of the blood relatively constant despite changes in food intake and excretion (gastrointestinal or urine for example) of various blood components throughout a 24 hour period is achieved, in part, with the aid of various sensors placed at specific locations throughout the device that measure the concentration of the substances that are being transported by the various components of the device. The information from the sensors is fed back to resident software that is programmed to make the necessary changes in the transport of specific substances by the device (through changes in the current, voltage, flowrates, and flow direction). Moreover, in the EDI components of the device, because multiple wafers with different selectivity are used, when certain wafer streams are taken offline, the relative ratio of the ions transported changes, thus allowing an additional level of control. Finally, physically adjusting the flow through the chambers, or in some embodiments altering the current to the electrodes, adds an additional level of control.

Because this device requires no dialysate and can normalize human blood chemistry despite changes in input and output, the device can function as an external or implantable artificial kidney. In addition, the device can function as a stand-alone unit and replace dialysis machines that are now used to dialyze patients.

BRIEF DESCRIPTION OF THE DRAWINGS

So that the above-recited features of the present invention can be understood in detail, a more particular description of the invention, briefly summarized above, may be had by reference to various embodiments, some of which are illustrated in the appended drawings. It is to be noted, however, that the appended drawings illustrate only some embodiments of this invention and are therefore not to be considered limiting of its scope, for the invention may admit to other equally effective embodiments.

FIG. 7A presents Table 1 which reports ion transport data obtained from several single wafer experiments conducted over a 24 hour period, and FIG. 7B presents Table 2 which reports total amounts of ions removed in the same experiments.

FIG. 8 additionally depicts the placement, in some embodiments, of additional sensors along the treatment flow path.

DETAILED DESCRIPTION OF THE INVENTION

Figure 1:
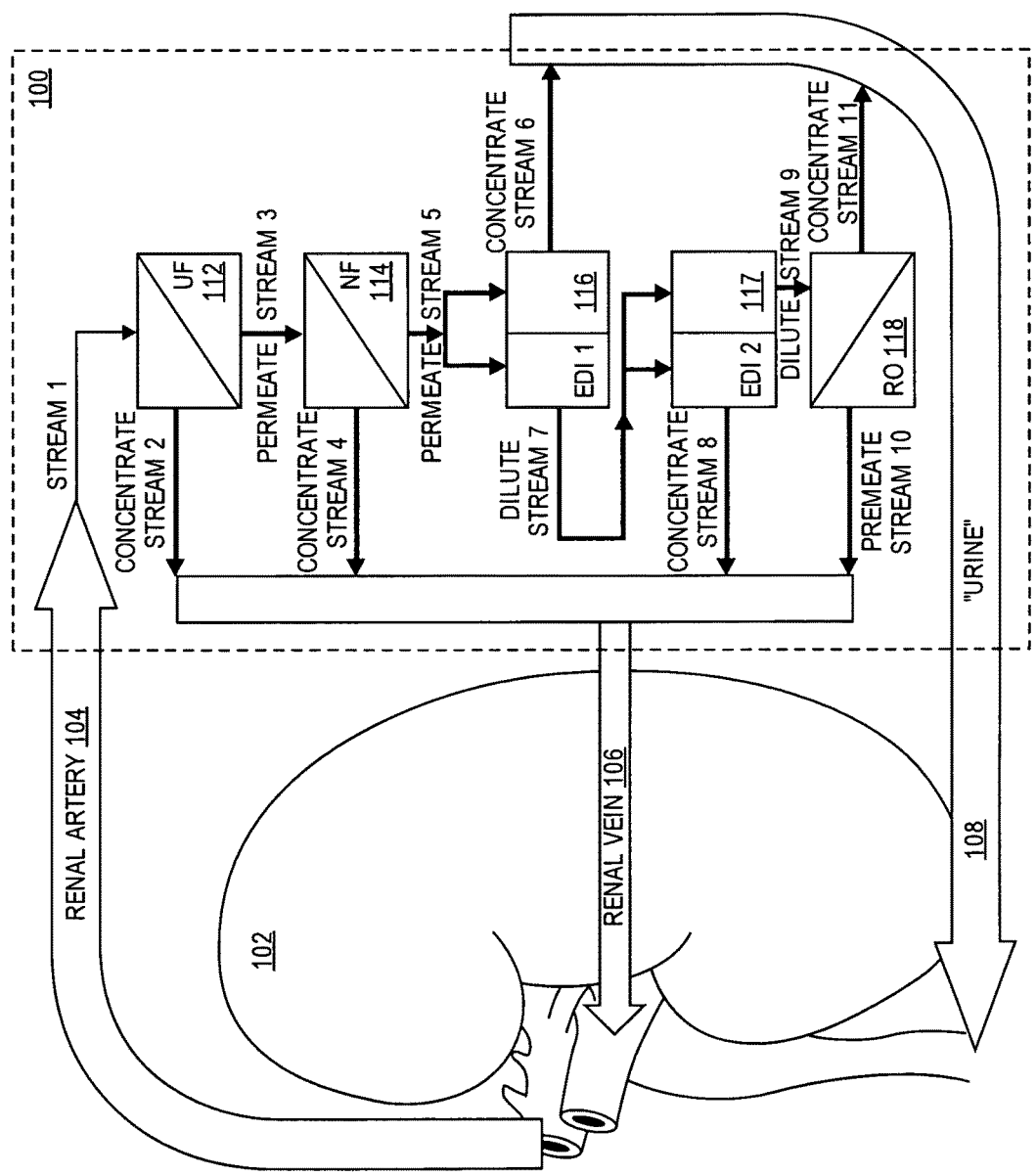
FIG. 1 is a schematic of an overall device for treating human blood, returning the treated blood to the blood stream, and the removed materials to the urine stream.

With reference to FIG. 1, the overall device 100 is shown within the dotted lines, the device comprising the following: (1) ultrafiltration (UF) unit 112, (2) nanofiltration (NF) unit 114, (3) electrodeionization (EDI 1 and EDI 2) units 116, and 117, and (4) reverse osmosis (RO) unit 118.

The purpose of ultrafiltration unit 112 is to separate out from an incoming blood stream (in the illustrated embodiment from renal artery 104 of kidney 102), red blood cells (RBCs), white blood cells (WBCs), proteins, and any other high molecular weight components for return to the blood stream via a fluid conduit to a vein, in the illustrated embodiment renal vein 106. The separation of these large components first from the smaller neutral (glucose, urea) and ionic components (sodium, potassium, etc.) of the blood also aids in the prevention of fouling in the other, downstream separation units.

Ultrafiltration itself is a well-understood membrane technology that uses pressure to force a fluid such as water through a semi-permeable membrane. With small pores, it is able to selectively retain proteins and cells while passing ions, sugars, and urea. Furthermore, through surface treatment such as with polydopamine or other hydrophilic surface coating, ultrafiltration is able to resist membrane fouling and thus useable for longer periods inside the body.

Some common ultrafiltration membrane materials include polysulfone, cellulose acetate, polyether ether ketone, etc. The standard operating conditions for these membranes are 10-100 psig with fluxes ranging from 20-200 gallons per $ft^2$ day. Using these assumptions as well as knowledge gained from membranes currently made for use in the artificial kidney of this invention, a prototype device was assemble to demonstrate proof of concept for removing proteins and cells that as a cube measured 8 inches on each side. Miniaturization of this section of the device is ongoing.

The purpose of the next component, nanofiltration unit 114, is to recover glucose from the incoming blood and send it back into the body through a vein, such as renal vein 106. Nanofiltration, like ultrafiltration, is a membrane technology that uses pressure to force a fluid such as water through a semi-permeable membrane. With microscopic pores and a dense diffusion layer, it is not only able to remove proteins and cells but also to selectively retain glucose while passing urea and ions.

Suitable nanofiltration membranes include those constructed from sulfonated polysulfone, aromatic polyamide, cellulose acetate, etc. The standard operating conditions for these membranes are 30-200 psig, with fluxes ranging from 10-100 gallons per $ft^2$ day. Using these assumptions and a membrane currently tested for use with the artificial kidney of the invention, a device was constructed for selectively removing glucose that is 10 inches on each side. Miniaturization of this this section of the device is ongoing.

The permeate stream from NF unit 114 is next directed through fluid conduits (i.e. tubing) in turn to EDI units 116 and 117 for selective transport of ions (potassium, sodium, etc.) that need to be removed from the body through "urine" stream 108. Electrodeionization is a charge driven membrane technique (described in more detail later on) that uses ion exchange resin wafers to facilitate selective ion transport. The units incorporate electrode arrangements that facilitate the turning on or off of ion flow across the wafers. By this flow control method, according to an embodiment of the invention, ions are selectively removed from the blood, something no other patented or published technique has been able to achieve.

Standard membrane materials suitable for use include nafion, sulfonated polysulfone, aminated polystyrene, etc. Operating conditions per cell pair (an anion and cation exchange membrane set) are normally around 5 volts, at 5-25 $mA/cm^2$. Using these assumptions, the two devices used in the artificial kidney device so far constructed have cube dimensions of 14 inches and 11 inches, respectively. Miniaturization of these sections of the device is ongoing.

Finally, dilute stream 9 from second EDI unit 117 is sent to reverse osmosis (RO) unit 118 to concentrate ions into the "urine" stream and return water (the permeate) to the body through a vein, such as renal vein 106.

Reverse osmosis, like the other separation technologies utilized herein is a membrane technology that uses pressure to force water through a semi-permeable membrane. With a dense structure, the membrane is able to remove everything from solution. Many of the common membrane materials for reverse osmosis include aromatic polyamide and cellulose acetate. The standard operating conditions for these membranes are 50-1000 psig with fluxes ranging from 10-50 gallons per $ft^2$ day. Using these assumptions, a device was made for the prototype device with dimensions of 8 inches on a side. Miniaturization of the device is ongoing.

Figure 2:
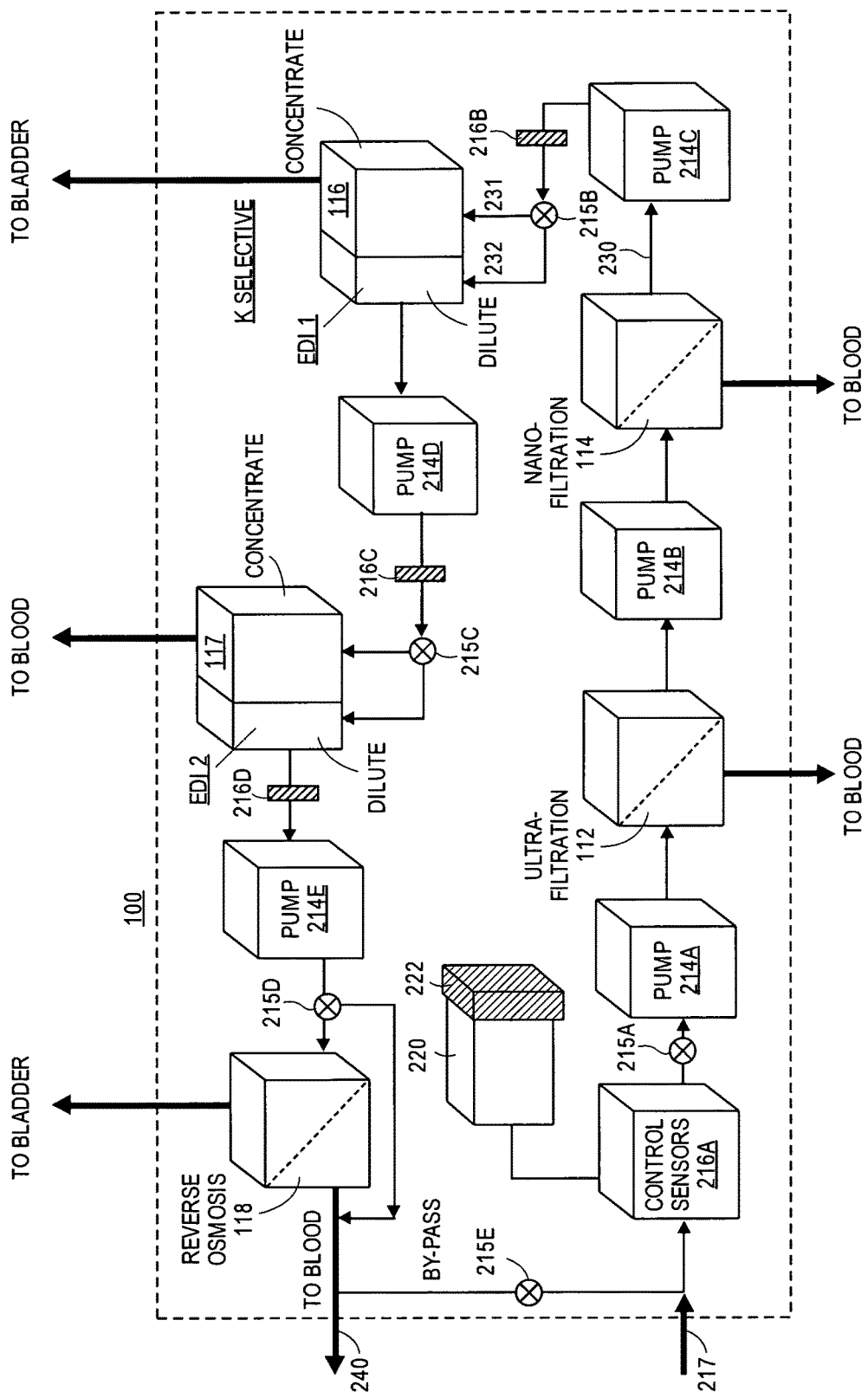
FIG. 2 is a more detailed schematic of the device of the invention, illustrating in some embodiments the incorporation of pumps wherein pressures within the system can be controlled.

All of the devices are further illustrated in FIG. 2, the system shown in more detail including one or more pumps 214(A-E), control valves 215(A-E) with others not shown, sensors 216(A-D) with others not shown, and control module 220. In one embodiment, the instant artificial kidney includes sensor module 216A inserted inline just after device entry port 217. The one or more sensors of the module in one embodiment are selected to measure the ion concentrations of interest (e.g. Na, K, Mg, Cl, phosphate) in the blood. In some embodiments, additional sensors are provided to measure blood ph, urea content, etc., all of which are connected to a control module 220 powered by rechargeable battery pack 222. These sensors are commercially available, off the shelf devices and are selected for their capability to work for long periods.

The device is designed to respond to changes in concentration in the blood of the ions detected. Resident software in control module 220 receives input from the sensor(s) to calculate the identity and relative concentration of the various ions. In response to changing ion levels, the software is programmed to direct flow to or bypass one or both of the EDI units. Alternatively it can be programmed to turn individual resin packed columns on or off within an EDI unit. Based on these readings, it is also possible to direct flow to or bypass a unit via control of one or more of valves 215 (e.g., valve 215D to bypass the reverse osmosis unit). Pumps 214 respond to pressure signals so as to keep flow at appropriate levels past the various membranes. Appropriate levels of pump pressure can be determined experimentally by measuring fluxes at different pressures and then designing in the appropriate amount of membrane area. Thus, even though ambient incoming blood pressure may in some instances be sufficient for the first ultrafiltration device, provision is made for adjusting pressures via pump 214A. As the nanofiltration device requires higher pressures, it too is provided with its' own pump 214B. The EDI devices should require no external pumps but in some embodiments, pumps 214C and 214D are provided. The RO unit also requires a separate pump 214E. One is able by control of the various pumps, bypass lines, and the like, to balance fluid flow through the overall device.

The EDI Units

Figure 3A:
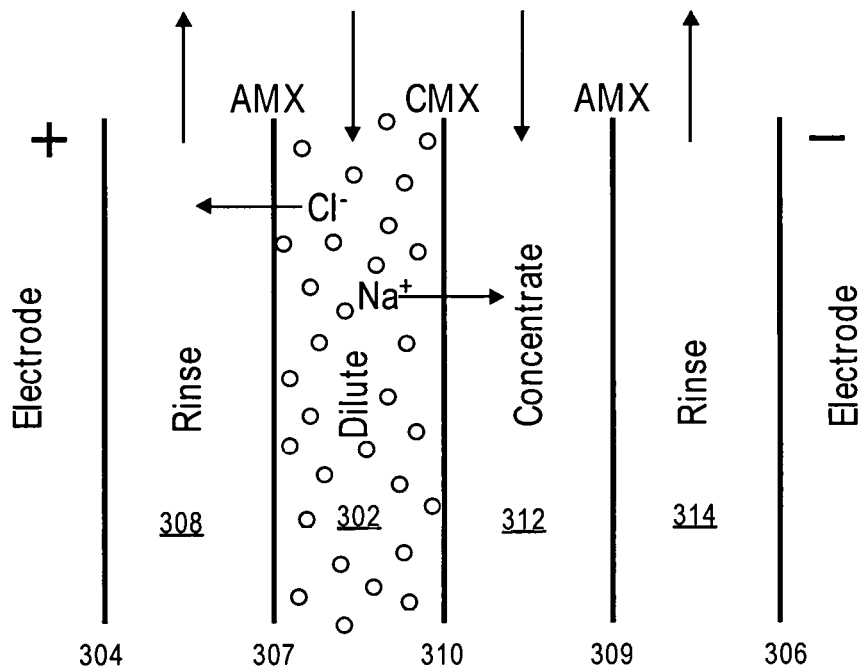
FIG. 3A is a schematic of a single dilute chamber EDI unit according to one embodiment of the invention.
Figure 3B:
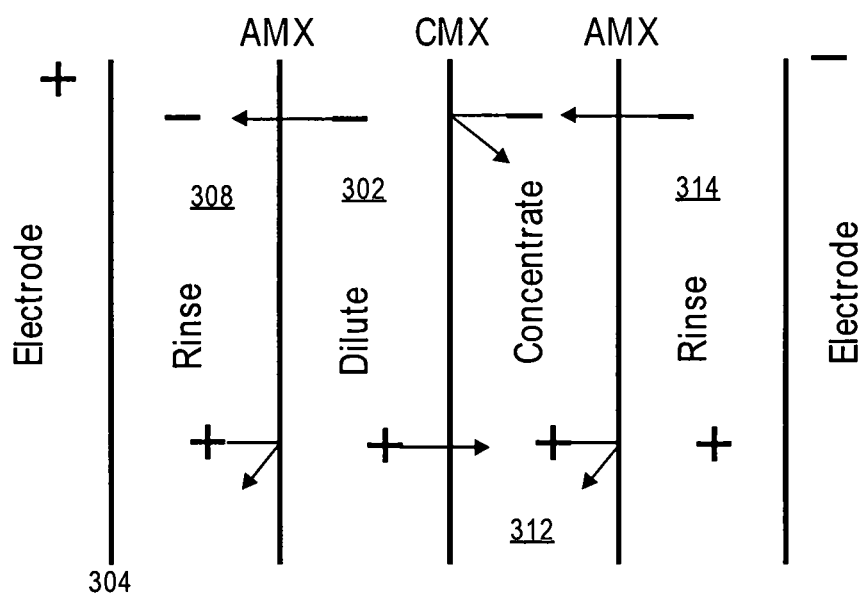
FIG. 3B is a schematic of the EDI unit of FIG. 3A, illustrating the movement of ions from one flow stream to another.
Figure 4A:
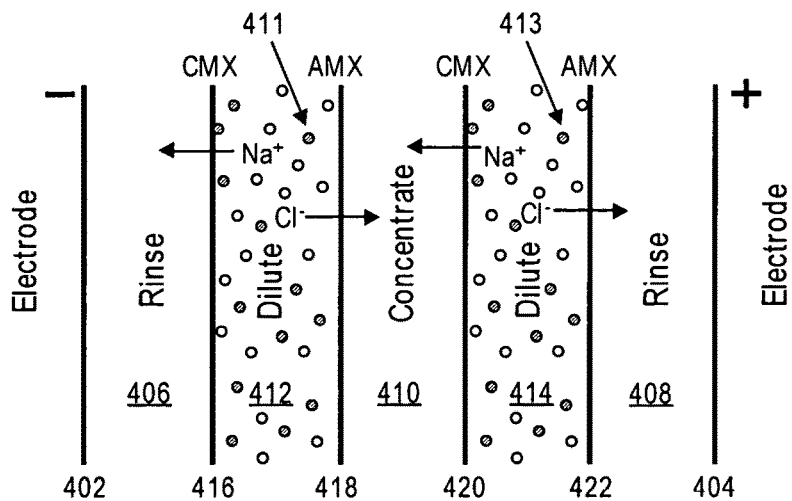
FIG. 4A is a schematic of a two dilute chamber EDI unit according to another embodiment of the invention.
Figure 4B:
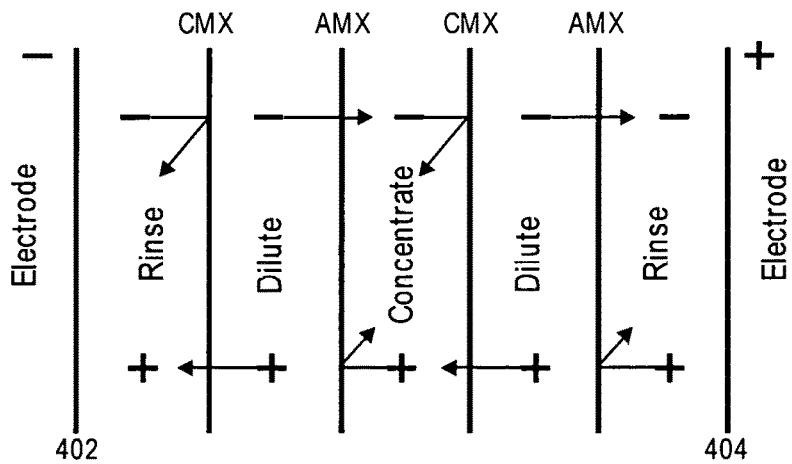
FIG. 4B is a schematic illustrating the movement of ions from each of the dilute chambers to other chambers across the various membranes of the unit.
Figure 5A:
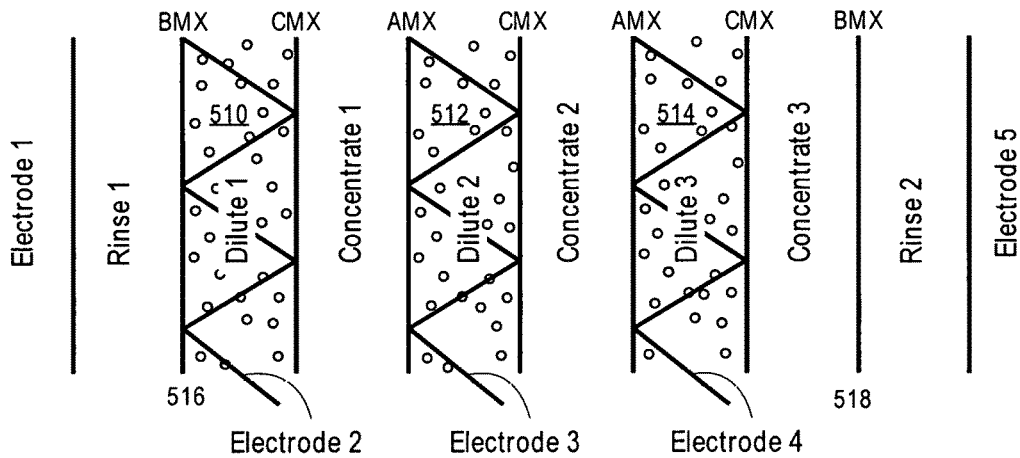
FIG. 5A is a schematic of an EDI unit similar to that of FIG. 4A, illustrating a device having three separate resin wafer filled dilute chambers, along with additional electrodes for controlling the on/off performance of each of the resin wafer filled chambers.
Figure 5B:
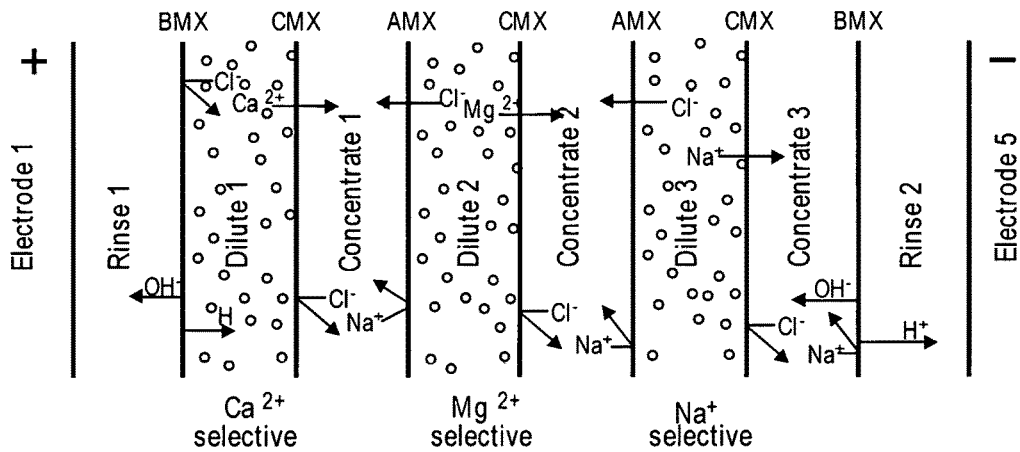
FIG. 5B is a schematic of the unit of FIG. 5A illustrating the various flow channels along with the flow paths of select ions between the channels.

The role of the EDI units 116 and 117 is to remove small, charged ions (Na, Cl, K etc.) from solution. This is done through ion exchange, the reversible interchange of ions between a solid (resin wafer) and a liquid. Electrodes are placed external to and on both sides of an EDI stack as illustrated in FIGS. 3A, 4A and 5A. Ions are allowed or prevented from moving through associated membranes based on their charge (FIGS. 3B, 4B, 5B). Positively charged ions are attracted towards the negatively charged electrode and the negatively charged ions towards the positively charged electrode. For example, cations (positively charged) transport through the Cationic Exchange Membrane (CMX), but are rejected by the Anionic Exchange Membrane (AMX), which only allows passage of the negatively charged anions.

In one embodiment, two EDI units are employed in series. This first EDI unit 116 is dedicated to the selective removal of potassium, the most critical of the ions requiring removal. This order of removal mimics the removal order of a fully functioning kidney. Removal occurs using resin wafers highly selective for potassium, such as, for example a mix of 50% Amberlite™ IR 120 from Dow Chemical, or a mix of 50% Amberlite™ IRA-402 from Thermo Fisher Scientific. These resins, having a demonstrated potassium selectivity of 5:1 or more, are also capable of removing other ions of interest, such as phosphates.

Due to the criticality of potassium ion removal, an additional in-line potassium sensor module 216B in an embodiment is positioned between NF unit 114 and first EDI unit 116, to both provide a check on concentration levels, and build in redundancy should the potassium sensor of module 216A fail.

For EDI 116, the exit (permeate) stream from NF 114 is split into two streams for passage through the first EDI unit. First input stream 232 is directed to the one (or more) resin containing dilute chamber(s). First stream 232 generally comprises about 90% by volume of input stream 230. The second flow stream 231 diverted to the one (or more) concentrate channel(s) constitutes the remaining portion (e.g. about 10%) of the feed stream. Generally, the split between the two streams will be 80-95% dilute to 5-20% concentrate. Flow ratios are controlled by adjustments to valve 215B, the degree of feed stream split determined by the control program of controller 220. In some embodiments flow split can be fixed through conduit sizing, thus eliminating the need for valve 215B.

This first EDI separation device, designed to remove just the one type of ion, need contain only one type of resin wafer. The unit can comprise but one, relatively large resin-wafer filled chamber through which the entire incoming dilute stream is directed. However, given miniaturization requirements, in some embodiments, unit 116 will include multiple, side-by-side resin wafer filled dilute chambers (such as illustrated in FIGS. 4B and 5B). In some embodiments, it will include just the one pair of encasing electrodes. In other embodiments, it may include additional, internal electrodes to allow the turning on or off the functional ion transport capability of the individual dilute stream chambers (e.g., as illustrated in FIG. 5A).

Second EDI unit 117, a multi-chambered unit, balances the other ions of interest by selectively transporting some or a larger portion of each of the ions by passing the dilute stream through various wafer resin columns, each packed with different resin wafers of different ion selectivity. In this unit, the goal is to maintain the same relative concentration of ions to be returned to the blood stream as is maintained by a healthy kidney. Thus, in some embodiments a third sensor module 216C is placed just upstream of second EDI unit 117. In other embodiments a forth sensor module 216D is placed just downstream of EDI unit 117 to monitor the effectiveness of treatment of the stream. In a communication feedback loop, controller 220 can turn on or off any of the resin wafer dilute columns by controlling the charge to the various electrodes within the EDI stack. Where column selectively is controlled using open/close valves, care must be taken to maintain overall device throughput. In one embodiment, as with unit EDI unit 116, the majority of incoming flow is directed to the dilute columns. In other embodiments, the flow may be more evenly split between dilute and concentrate, or otherwise adjusted by means of control valve 215C.

In the embodiment illustrated at FIG. 1 (see also FIGS. 2 and 8), EDI unit 2 acts as an ion absorber, where specific ions are transported across the various membranes to the concentrate streams, and these concentrate streams are returned to the blood. In this instance, what is quantitated is how much of each of the ions of interest need to be removed from the dilute stream and returned to the blood such that the amount of each of the ions remaining in the dilute stream are excreted from the body by the urine stream. When the dilute stream with the ions from EDI2 that weren't absorbed reach the reverse osmosis unit, essentially all of the ions in this stream are rejected by the reverse osmosis membrane whereas the required amount of is water absorbed and returned to the blood, leaving the appropriate amount of each ion and water that are remaining in the stream to be excreted in the urine stream. In another embodiment, flow from the dilute streams could be returned to blood, with flow from the concentrate streams sent to RO unit 118, Such reversal of flow paths, however, would require additional adjustments.

An exemplary Wafer Enhanced Electrodeionization (WE-EDI) unit is depicted at FIGS. 3A and 3B, the removal unit having but a single resin wafer stack 302. The resin wafer of this WE-EDI system facilitates selective ion removal, in the case of EDI 1 (116), potassium (K). The ion exchange resins increase the transport of ions at low concentrations. This occurs because the presence of the wafer increases the number of transport sites for diffusion.

As shown at FIG. 3A, packed immobilized resin wafers are located in feed compartment 302 of the EDI cell, with external electrodes 304 (charged positively) and 306 (charged negatively) shown. These electrodes, which may form or be affixed to the outer walls of the unit, comprise solid sheets or plates, and in some embodiments are designed to contain the fluids within. The AMX membrane 307 allows for the passage of negative ions into rinse channel 308, and CMX membrane 310 allows positive ions, in the case of first EDI unit 116, potassium ions, to flow from dilute stream 302 to concentrate stream 312, which concentrate is discharged to the urine stream. The processed dilute stream 302 is transported via suitable fluid channel from EDI unit 116 to the second EDI unit for additional ion removal.

In the unit of FIG. 3A, ions were allowed to flow though AMX membranes 307 into rinse stream 308. No attempt was made in the first prototype to keep the rinse stream ion free, which would not be the case in an operational unit (such as depicted in FIGS. 5A and 5B).

In one embodiment, the rinse channels (308 and 314) serve not only to isolate the electrodes from the dilute and concentrate channels, but serve to prevent corrosion of the electrodes as well. The rinse stream is part of a self-contained, closed loop system, the rinse liquid being for example 0.5-3 molar NaCl, or 0.2-2.0 molar $Na_2SO_4$, is provided to the unit from a rinse reservoir (not shown). Other rinse liquids such as potassium chloride, potassium nitrate, or other high concentration salts may also be used.

Since the driving force for ion transfer is electric charge, rather than concentration driven, the streams can flow past one another in any flow direction. Thus, the dilute and concentrate streams can flow in the same direction. The rinse streams can flow in the same or different directions relative to the streams adjacent.

FIG. 4A illustrates a two dilute chamber containing device with columns 412 and 414 packed with a different ion selective resin wafer. The EDI unit of FIG. 4A likewise is a schematic of a prototype unit. With the prototype, ion contamination of the rinse stream was not a concern. In a working system, especially an implantable one, the rinse stream (here streams 406 and 408) are kept as free as possible of transported ions. For such a unit, a second, concentrate stream (such as illustrated in FIG. 5A) can be provided between rinse stream 408 and dilute stream 414 (similar to that depicted in FIG. 5A). In a fully functioning embodiment, CMX membrane 416 and AMX membrane 422 of the prototype unit defining the rinse channels are replaced with bipolar ion membranes, which membranes act to reject both cations and anions, thus preventing ion contamination of the rinse streams.

Figure 4C:
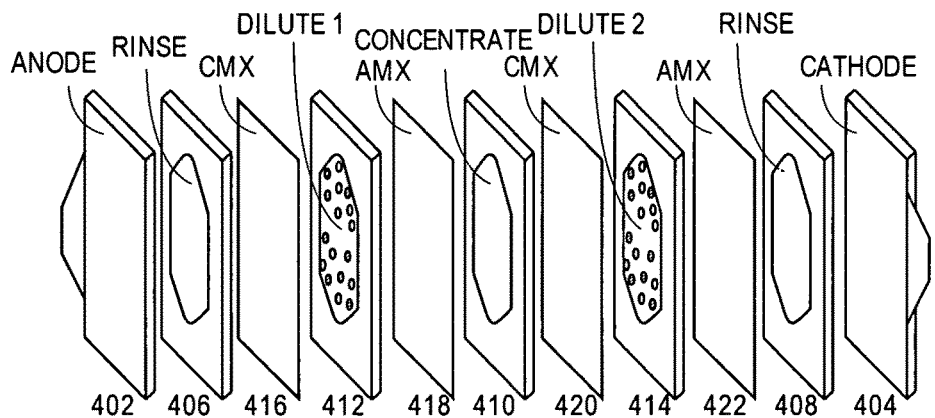
FIG. 4C is a three dimensional representation of the various membranes and flow channels within the EDI unit of FIG. 4A.

FIG. 4C is an exemplary schematic of the assembled EDI stack of FIG. 4A. The stack has alternating membranes, disposed parallel one to the other, with flow channels/chambers defined by spacers and resin wafer sheets. Resin wafer sheets 412 and 414 are made by pressing together ion exchange beads and a suitable biocompatible polymer binder, such as polyethylene, polypropylene, nylon, and the like. Using different resins in each of the activated flow paths, different selectivities are provided in a single device. Inlet and outlet manifolds (not shown) are used to direct the split dilute and concentrate flows both into and out of the various channels of the EDI device.

With reference to FIG. 5A, an EDI device is shown including 3 dilute streams 510, 512, and 514, exterior electrodes 1, 5, and porous interior electrodes 2, 3, and 4. In some embodiments, the interior electrodes comprise wire mesh screens, which (as illustrated) are incorporated into the resin wafer matrix of the dilute channels. In other embodiments, these electrodes comprise wire mesh screens placed on either side of each of the BMX, CMX or AMX separation membranes. In either of these embodiments, similar on/off functionality can be achieved by appropriate charging of the electrodes.

In the majority of cases, the EDI device of FIG. 5A operates with electrode 1 and 5 on, electrode 1 in some embodiments charged positively and electrode 5 charged negatively. Outer flow chambers through which rinse streams 1 and 2 run is part of a closed circuit with the rinse streams having no access to the host body or other of the device streams. Bipolar membranes (BMX) 516 and 518 prevent ion transport from the other streams to or from the rinse streams. Flow entering the system though the input manifold (not shown) is split into dilute streams 1, 2, and 3 (the streams recombined upon exiting the EDI unit for further processing) and concentrate streams 1,2 and 3 (which are later recombined for discharge to blood). In normal operation, the system selectively removes the targeted amount of sodium (Na), Magnesium (Mg), and Calcium (Ca), responding to detected changes in the concentrations of these ions.

In some embodiments, if excursions from normal are small in EDI unit 117, the unit can be ran for shorter periods of time, such as by shunting flow to a bypass line (not shown). Alternatively, one or more of the EDI columns within the unit can be virtually bypassed without having to divert flow. This is achieved by changing the charge applied to certain of the various electrodes of the EDI stack. In some embodiments a voltage can be applied more than two electrodes at a time, in which case it is preferable to add a second, independently operable power source.

By way of example, for second EDI unit 117 if less sodium need be removed from the incoming dilute stream, electrodes 1 (+) and 4 (−) are charged rather than of electrodes 1 (+) and 5 (−). In this configuration, dilute stream 514 no longer acts as a selective separation stream for Na, and thus less sodium is removed, dilute stream 514 now serving as a virtual "rinse stream". The same methodology can be applied to reduce calcium selectivity, i.e. by charging electrodes 2 (+) and 5 (−) while bringing all other electrodes to ground. Magnesium selectivity is achieved by jumping between electrode pairs 1 (+) and 3 (−) and 3 (+) and 5 (−), the other electrodes taken to ground potential, thus effectively taking the magnesium selective dilute stream 516 offline, while continuing to remove sodium and calcium.

Other combinations of electrode charging can be employed to functionally turn each of the various dilute columns on or off. In one embodiment, if all ion concentrations are within normal limits, unit 117 can be effectively bypassed, while maintaining the same flow split between the dilute and concentrate channels, by bringing all electrodes to ground. In this embodiment, no downstream adjustments of flow are required. While the same result can be achieved using a bypass line (not shown), adjustment of the RO unit may be required in order to account for increased incoming flow.

Similarly, in the case of first EDI unit 116, if potassium levels are within normal ranges, virtual bypass can be achieved by simply turning off power to all of the device electrodes.

As shown in FIG. 5B, $OH^-$ ions generated by BMX membrane 516 migrate to rinse 1, while on the far side of the device $H^+$ ions generated by BMX membrane 518 migrate to rinse stream 2, the bipolar membrane causing water in dilute streams 510 and 514 to split. These $OH^-$ and $H^+$ ions later recombine in the rinse reservoir to form water.

In some embodiments, second EDI unit 117 can comprise multiple, separately functioning modules, each module including two or three dilute streams. In the case of a 2-dilute channel module, two modules can be stacked one next to the other, separated by an insulator, for the controllable separation of up to four different ions. A third module similarly stacked can provide for up to six separately selective dilute streams. Flow through the various dilute streams in each case may be controlled, on the one hand by appropriate valving, and on the other hand by control of the charges applied to the various electrodes of the several EDI modules. In some embodiments, each EDI module may comprise three selective dilute streams, providing a total of from 6 to 9 separate dilute streams depending upon the number of EDI modules used in the EDI device. In some embodiments, both first EDI unit 116 and second EDI unit 117 can be of the same general construction, though with dilute columns filled with different resin wafers.

Partial or Total System Bypass

The unit is designed with built in excess capacity, such that it will likely need to be on line only about half the time. Accordingly, it will not always need to be treating blood. Thus, while the device of this invention is designed to perform continuously, 24/7/365, from time to time it may be appropriate to bypass one or more of the treatment units, depending upon blood content and concentrations, as well at times bypass the device entirely. Thus, when the sensors of module 216A determine that incoming blood chemistry is within normal limits, flow can be diverted from inlet 217 directly to outlet 240 via a bypass conduit, in some embodiments by closing off valves 215A and 215D, and opening valve 215E, In this mode, all flow bypasses unit 100.

In another embodiment, virtual bypass can be achieved by turning off pump 214A. In this mode, at ambient pressure practically no separation occurs in ultrafiltration unit 112, and thus almost all flow entering the unit is returned to the blood stream. Similar bypass can be achieved in NF unit 114 by simply turning off pumps 214A and 214B.

Sensors/Control Mechanisms

As previously noted, sensors are used to monitor the concentrations of components including glucose, sodium, chloride, and potassium.

In some embodiments, a sensor module 216A is placed at the intake of the system, at a location upstream of first ultra-filtration unit 112. This module 216A can have one or more sensors, such as micro fluidic sensors and the like, that can detect the concentrations of neutral (glucose, urea) and ionic (sodium, potassium, etc.) components in real time. Suitable types of sensors include potentiometric (measures charge potential) electrodes and electrochemical biosensors. The electrochemical biosensors can consist of enzyme based interaction where concentration levels are based on real-time detection and high selectivity for neutral components such as glucose, urea etc. Additionally, electrochemical sensors with amperometric devices (measure current produced by biochemical reaction in device) can be utilized to potentially detect oxygen concentration based on change in current such as the Clark oxygen electrode. An example of a specific sensor system for ions such as Na, Ca, Mg, Cl and K include the Libelium Smart Water Sensor with varying sensor probes for each ion. Overall, the sensors will include means to periodically calibrate themselves, and to communicate with the controller.

In some embodiments the sensors can be located immediately upstream of the unit to which the collected information is relevant for the control of flow through the unit. Thus, for example, in the case of the EDI units, sensor module 216B selected for measurement of K+ ion concentration in the blood stream can be located immediately upstream of first EDI unit 116. If potassium concentrations are high, the dilute blood stream can be directed to this unit, and from there the exit dilute stream directed to second EDI unit 117. If the concentration of potassium is below actionable levels, the control program resident in controller 220 (programmed to open or close a bypass valve) can bypass the first EDI unit, sending the dilute stream directly to second EDI unit 117. In other embodiments, the concentrations of ions leaving the units are monitored. In other embodiments, additional sensors can be place after each separation unit to monitor the effectiveness of the unit to obtain the targeted separation levels.

The Controller

Controller 220 for the implantable kidney device of the invention is a virtual minicomputer, containing all the software and firmware necessary for independently operating the device. It will include software for converting sensor outputs, and calculating ion concentrations, and among other things controlling operation of the pumps, valves and EDI unit electrodes in response to sensor readings. It is designed for communication with external devices such as an RFID reader, a computer, etc. using well-established communications protocols such as Wi-Fi, blue tooth, ZigBee, and the like. Additionally, software and electronic hardware of the controller allow for the programming and reprogramming of the device from an external source, thus allowing for the updating of the operational program, as required. Resident software may also include health monitoring programs for tracking the health of the various device components as well as the health of the user, with the capability for electronically issuing appropriate warnings/alerts to a patient's physician, device monitoring service, or other designated provider of possible, probable or actual part failure, or a serious blood composition excursion.

Unit Power

For fully autonomous operation, the kidney device of this invention requires its own, separate power source for the running of both the electronic and mechanical components of the system. Generally, the electronic components of the device, such as the controller, sensors, and the mechanical components such as pumps and valves are collectively believed will require DC battery sources capable of supplying of between 5 to 100 watts. Battery pack 222 in one embodiment is located adjacent the controller. In another embodiment it may be placed anywhere within the overall device envelope. Suitable batteries for the device are those capable of easy recharge. In the implantable kidney, the battery pack should be capable of recharge through the skin from an external source, such as an external RFID source.

The system can also include software for monitoring the state of charge and health of the batteries, and necessary circuits and software to facilitate remotely recharging the battery pack.

Flow/Flux/Pressure Though the System

For proper device operation, a constant fluid flow through the system is maintained, one that matches the blood flow rate of the artery or vein to which the system is connected. Thus, it is necessary to control fluid flow rates through each of the units, such as through sizing of the separate units, and/or pressures maintained within the units whereby the combined discharge flows matches flow from the input blood stream, notwithstanding differences in optimal operating pressures and fluxes of the individual units.

Ambient blood pressures are to be taken into account in setting the optimal operating pressures for a particular device, as pressures will vary with the location of the vein or artery to which the device is connected. For example, in one option, the device might be inserted through a double lumen catheter into the subclavian vein towards or in the right atrium. Here, the central venous pressures are about 2-6 mm Hg (0.04-0.11 PSI) with a flow rate of approximately 1 liter/min. In another option, the inflow to the device could be from one of various arteries (iliac, or renal for example) and the outflow to one of several veins (iliac vein, renal vein). The pressure in the renal and iliac arteries is approximately 100 mm Hg (1.93 PSI) with a flow of approximately 500 ml/min. The pressure in the renal vein is approximately 1-5 mm Hg (0.02-0.10 PSI) with a blood flow rate of approximately 500 ml/min.

Given the pressure requirements of the ultrafiltration, nanofiltration and reverse osmosis units, means are provided to increase the pressure differentials across the various separation membranes to between 10-30 psig and 10-50 psig respectively. In some embodiments, pressures are controlled by constriction and expansion of the flow channel diameters leading into and from these devices. In other embodiments, pumps can be used to provide the internal pressures required for effective device operation. As illustrated at FIG. 2, pumps 214(A-E) can be provided immediately upstream of each separation unit.

Whatever the operational pressures of each of the devices, and the flow to and from the devices, the overall output of all streams must match the input of the artery or vein to which the kidney device is connected. This flow-balancing is an important design requirement in sizing the various elements of the device, and the connecting fluid channels within the device. While flow rates can generally be designed in and thus fixed for a particular system, provision can be made for fine tuning of flows within the device so as to maintain the required input-output matching.

System Placement

The system is intended to be self-contained, ultimately sized for placement within the human body. Where the system is to be connected to a vein such as a renal vein, pumps within the unit provide the pressures required to drive the various fluid streams through the various filter membranes. Should the system be connected to an artery, arterial pressure may be sufficient to accomplish this without the aid of pumps. Whether or not to implant the device, and if implanted to connect it to an artery or a vein is a medical decision, the criteria for which is beyond the scope of this patent The Prototype System A prototype device was assembled on a bench scale basis. The miniaturization required to reduce the size of the unit to a device measuring about 6 cubic inches is ongoing. The prototype, as described below, was built to demonstrate proof of concept.

Prototype Ultrafiltration Unit

For ultrafiltration unit 112, UF membranes were produced by hollow fiber spinning and were composed of 17.8% polysulfone. Hollow fiber membranes are described in literature. For this process, one can use almost any of these hollow fiber membranes as well as any surface treatment process to reduce fouling. The constructed device is unique to the inventors' laboratory but any miniaturized device of hollow fiber can be used for the first step of this process.

The hollow fibers described above were tested for potential tears within the membranes by embedding the fibers in water and running $N_2$ gas through each fiber. The fibers with no leakage were placed in 100% ethanol for 6 minutes to 72 hours. Then the fibers were dried and the ultrafiltration unit was constructed using two elbows, a tee and connector tubing. The fibers in the elbow region were embedded in epoxy glue in order to manufacture a crossflow filtration and separate the feed, permeate and retentate flows. To decrease fouling, the membrane surfaces were modified using polydopamine (PDA). Before coating, 100% ethanol was used to wash the fibers for 30 minutes at 0 psig with pump dial speed of 2.5. The fibers were then washed with di-water for 1-2 hours at 0 psig with pump dial speed of 2.5. Dopamine hydrochloride (0.3-0.5 mg/mL) in 10 mM Tris-HCl (pH=8.6) solution was stirred at 25° C. for approximately 4-5 hours. The PDA coating was applied to the membranes for 3-5 hours at 0 psig and pump dial speed of 2.5. After coating the fibers, di-water was used at 0 psig for 1 hour to wash away excess PDA solution. In addition, some preparation also used a 50 mM HCl rinse at 0 psig for 20 minutes. Next, air was pumped for 1-2 minutes and the unit let dry overnight. Each unit was tested initially using di-water at different pressures. In order to evaluate the membrane's potential for rejecting RBCs, WBCs, and proteins, two model proteins (IgG and BSA) were tested. A solutions of 3.2 g/L BSA or 0.75 g/L IgG was prepared in PBS (pH=7.4) with 0.02% sodium azide.

Prototype Nanofiltration Unit

For nanofiltration unit 114, a Sterlitech HP4750 stirred cell was utilized with a polyamide thin film composite flat-membrane that consisted of an area of 19.63 cm$^2$. A solution of about 250 mL was stirred at 200 RPM at room temperature and pressurized with nitrogen gas at 30 psig. The NF solution was composed of 2.85 g/L sodium, 0.16 g/L potassium, 0.02 g/L magnesium, 0.095 g/L calcium, 3.72 g/L chlorine, 0.10 g/L urea, 0.01 g/L creatinine, and 1.00 g/L glucose. A DNS (3,5-dinitrosalicylic acid) assay was used to determine the rejection of glucose by the membrane. Briefly, 1 g of DNS was added to 100 mL of 2N sodium hydroxide that was heated and stirred until completely dissolved. Another solution was made by combining 100 g of sodium potassium tartrate with 250 mL of boiling water. These two solutions were combined while still hot. This DNS mixture was stored in a dark bottle at 4° C. For analysis, 1 mL of the DNS mixture was combined with 1 mL of solution and diluted with di-water to a final volume of 10 mL. The sample solutions were then boiled for 6 minutes, allowed to cool on ice, and analyzed using a NanoDrop spectrophotometer at 470 nm and the concentration was calculated by comparison with a calibration curve. A glucose rejection value of 99% was achieved.

Experiments for the prototype nanofiltration unit were conducted at a pump dial speed of 2.5 at room temperature with a stirrer setting of 200 RPM. The retentate and feed pressure were determined by the water experiments where the range was between 30-45 psig for both the BSA and IgG experiments. Flow rates were determined for both permeate and retentate streams using change in volume for a certain timeframe. At each time point, sample concentrations were determined using a NanoDrop spectrometer at 280 nm. Results were evaluated by calculating the rejection, which correlates to the amount of material retained by the membrane. Rejection was calculated as follows: Rejection=$(1-C_{permeate}/C_{feed})100\%$ where $C_{permeate}$ is the concentration of the measured component that passes through the membrane and $C_{feed}$ is the concentration of the measured component fed to the membrane. For BSA a 94% rejection was achieved and for IgG a 95% rejection was achieved.

Atomic absorption was utilized with an air-acetylene tank (40-45 psig air, 10-15 psig acetylene) to determine the rejection of ions such as sodium and potassium. For sodium, the sample was diluted 50× using di water and the absorption wavelength was 330.2-330.4 nm with a lamp current of 5 mA. For potassium, the sample was not diluted and the absorption wavelength was 404.4 nm with a lamp current of 6 mA. Typically, no ion rejection was observed for the NF membranes.

To determine the urea concentration, Sigma Aldrich Urea Assay Kit was utilized in conjunction with a NanoDrop spectrometry at 570 nm. The reaction was carried out according to the kit protocol and incubate for 60 minutes at 37° C. before testing on the spectrometer. When necessary, the sample was diluted to fit the calibration curve. Typically, no urea rejection was observed for the NF membranes.

Nanofiltration membranes have been described in literature. For this process one could use almost any of these nanofiltration membranes as well as any surface treatment process to reduce fouling. The operation of these membranes could be in flat sheet or hollow fiber form. For this prototype, a flat sheet form was employed.

Ion exchange wafers used in experimentation were composed of both anion and cation exchange resins (seventeen different wafer combinations tested thus far, the results of which are reported at the tables 1 and 2 of FIGS. 7A and 7B), polymer (polyethylene powder, 500 micron), and sucrose. The polymer is used to bind the resins together, and the sugar used to create porosity in the wafer. A custom iron cast was constructed (127 cm×127 cm diameter). Each batch of wafer ingredients were mixed in a 23:23:15:10 gram ratio of anion-resin:cation-resin:sugar:polymer. The composition was then mixed at a rate of 300 rpm for 5 seconds using Flacktek Inc. SpeedMixer (model: DAC 150 SP) to enhance uniformity throughout. Wafer material was spread in cast, and then inserted into a Carver Press (model 3851-0), and run at 10,000 psi and 237 degrees F. for 90 minutes, followed by a 20 minute cooling period via pressurized air treatment. After cooling, the cast was removed, and wafer carefully extracted. Each casting made roughly 4-5 individual wafers for insertion into various chambers in the EDI cell. The wafer material is then soaked in deionized water for at least 24 hours. This allows the sugar to dissolve out, and create the pores in the wafer.

Prototype EDI Units

For the EDI two 500 mL beakers are filled 400 mL of 0.3M NaSO4 solution. These are the rinse reservoirs. Another breaker, the dilute reservoir, is filled with 400 mL of a blood-like ion solution. (0.29 g/L of Potassium Chloride, 5.6 g/L of Sodium Chloride, 0.34 g/L of Calcium Chloride Dihydrate, 0.02 g/L of Magnesium Chloride Hexahydrate, 0.08 g/L of Sodium Phosphate Monobasic Anhydrous, 0.1 g/L urea, 0.01 g/L Creatinine Hydrochloride, and 2.1 g/L of Sodium Bicarbonate), and a final beaker, the concentrate reservoir, is filled with 400 mL of 2% Sodium Chloride. The solutions in the reservoirs are pumped into the EDI cell of FIG. 4A Power was supplied by clamping positive and negative leads to the electrodes. The power supply is turned on and set to a constant current of 0.02 Amp. The voltage was kept between 2-7 V and 50 mL samples were collected from all four streams at 0, 3, 6, and 24 hours. The voltage, current, conductivity, approximate volume, and flow rate were all recorded at these times. Samples were analyzed using Ion Selective Electrodes (Chloride and Bicarbonate), an assay kit (Phosphate), and flame spectroscopy (Sodium, Potassium, Calcium, and Magnesium) through an Atomic Absorption machine.

For the reverse osmosis (RO) membrane filtration, a Sterlitech HP4750 stirred cell was utilized with a membrane area of 19.63 cm$^2$. A solution of up to 250 mL was stirred at 200 RPM at room temperature and pressurized with nitrogen gas at 20 psig. The RO solution was composed of 78 mg/L sodium, 6.7 mg/L potassium, 0.67 mg/L magnesium, 2.83 mg/L calcium, 78.75 mg/L chlorine, 403 mg/L urea, 53 mg/L creatinine, and 47 mg/L glucose. The analysis of glucose and urea were determined using the same methods described in the NF section. Atomic absorption was utilized with an air-acetylene tank (40-45 psig air, 10-15 psig acetylene) to determine the rejection of ions such as sodium and potassium. For sodium, the sample was not diluted and the absorption wavelength was 330.2-330.4 nm with a lamp current of 5 mA. For potassium, the sample was diluted 5× with di-water and the absorption wavelength was 769.9 nm with a lamp current of 6 mA. Rejection values achieved for the different ions are as follows: 96% (sodium), 93% (potassium), 89% (chloride).

Many different RO membranes are used in literature including aromatic polyamide, cellulose acetate, cellulose triacetate, etc. All of these membranes could be used in the system of this invention.

Alternative Unit Arrangements

Figure 8:
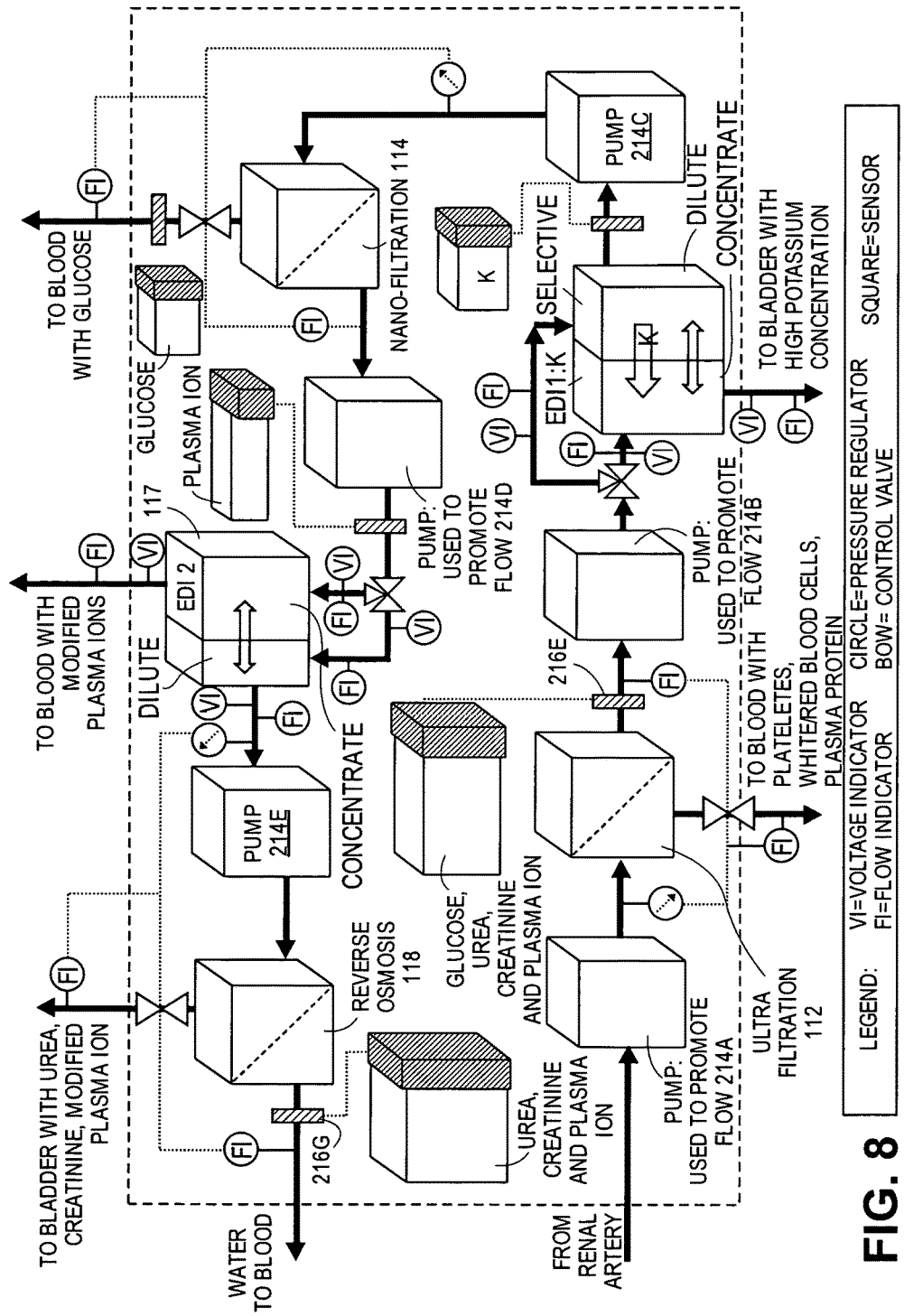
FIG. 8 includes is a schematic of an embodiment of the invention, similar to that shown if FIG. 2, in which the order of the nano-filtlration and the first electrodeionization unit is reversed.

In an embodiment of the invention, illustrated in FIG. 8, the first EDI unit can be positioned immediately after the ultrafiltration unit and upstream of the nano filtration unit. In this embodiment, like with the first embodiment, the ultrafiltration unit is designed to remove proteins and cells from the system, these components re-introduced into the blood stream. Everything else goes through the membrane and on to the other units for further processing.

The first EDI unit, is loaded with resin wafers selected for the preferential removal of potassium. It is to be noted that these same resin wafers also remove phosphates, and thus in one embodiment no separate phosphate removal column is required.

This switching of the treatment order between the NF and first EDI unit is necessitated in some embodiments by the fact that certain of the most readily available and inexpensive nano filtration membranes are prone to reject phosphates. That is, by retaining phosphates as well as glucose, the NF system returns both components to the blood, thus eliminating the overall system's ability to remove phosphates. By inserting the potassium specific EDI unit first, ahead of the NF unit, this problem is avoided. In other embodiments, in which a phosphate accepting nano filtration membrane is selected, one that allows phosphates to pass through, can be substituted, thereby eliminating the need for order switching.

The EDI units, as previously described can have serval ion exchange wafers in its several chambers. These ion exchange wafers have the ability to selectivity remove different ions as shown in Table 1 of FIG. 7A. Thus, by way of example, by employing wafers selective for potassium which are also (though not reported at FIGS. 7A and 7B) selective for phosphates, allows for the separation of these components in this first unit.

With reference to FIG. 8, this figure is similar to FIG. 2 with the exception of the positioning of the NF unit 114 after first EDI unit 116, as well as the depiction of additional sensors and control mechanisms.

Experimental Results

Figure 6:
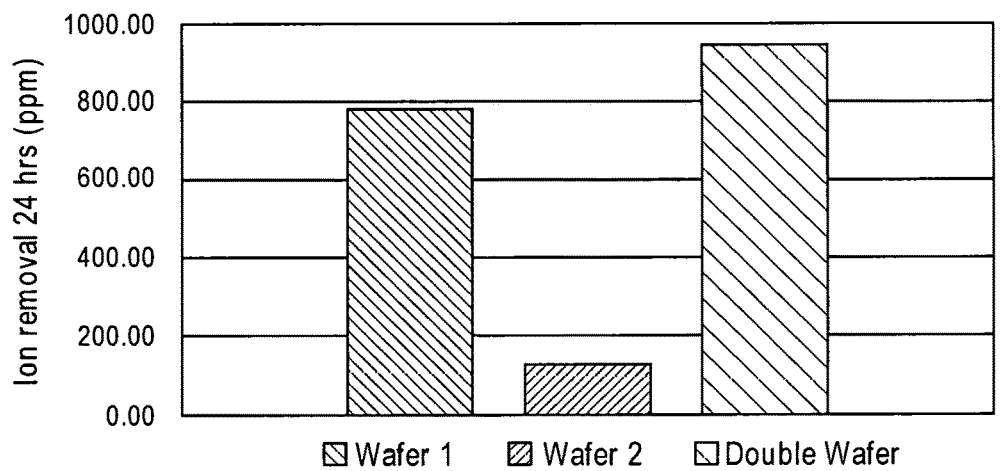
FIG. 6 is a plot of data obtained from a double wafer filled chamber experiment.

FIG. 6 shows the result of one double wafer experiment with a single ion. Here, two wafer types were used in two separate dilute chambers as would be performed in the artificial kidney. The basic set up of the two-wafer EDI system is similar to the single wafer. Again, the anionic exchange membrane (AMX) transports anions and the cationic exchange membrane (CMX) transports cations. The circles 411 and 413 in the dilute chambers of FIG. 4A indicate the immobilized resin beads. The different shades (light/dark) indicate that the wafers are composed of different beads in the different chambers. The ionic transport mechanism is the same in the double wafer as the single wafer system, as described above. The wafer fabrication procedure, and the experimental procedure are the same as well.

As shown in Tables 1 and 2 of FIGS. 7A and 7B, the selectivities for the different ions change with the different ion exchange wafer compositions. While the individual selectivity of a particular ion may be higher or lower than a human kidney, an overall EDI system can be built from the combined wafers that replicate the separation abilities of the human kidney without a dialysate. For Table 1, various resin compositions and types of resins were used to create the immobilized resin wafers. The table shows how the different resin compositions and resin types facilitate varying ionic affinity. The table is normalized to sodium (Na$^+$). Each value listed is the amount of ions that will be transported whenever one Na ion is transported. For example, wafer 1 will facilitate the transport of 1.65 potassium (K$^+$) ions for every 1 Na+ ion that is transported out of the solution and through the resin wafer.

Table 2 lists the various resin compositions and resin types and their differing amounts of ionic transport. The values shown is the difference in ionic concentration between hour 0 and hour 24. The reported values equal to the amount of ions (in ppm) that were transported (removed) from solution over a 24-hour period. For example, using wafer 1, 2572.15 ppms (or mg/L) of Na+ was removed from solution in 24 hours.

CONCLUSION

Though the system is presently at an early stage of development with miniaturization ongoing, the system will initially be employed entirely external to a user's body. This is to insure operability reliability before the unit is implanted in whole or in part. Once proven, the system, will be miniaturized to the point it will be small enough for partial or complete implantation, and positionable in one of several locations within the human body. By way of example, the unit could be placed in the human body proximate to an existing kidney (healthy or diseased) or in place of a removed kidney(s) intra-abdominally. In some embodiments, certain subcomponents could be placed subcutaneously with the remainder situated externally. In other embodiments, certain subcomponents could be placed subcutaneously with the remainder situated intra-abdominally. In still other embodiments, certain components could be placed externally, certain components subcutaneously, and certain components intra-abdominally. In yet other embodiments, subcomponents could be placed externally with the remainder situated intra-abdominally. The ultimate placement of the device, or the decision as to which components are placed internally and which externally for a given patient is a medical one, the criteria for which is beyond the scope of this patent. It is to be appreciated with all of these possible variations that each is in accord and within the scope of the present invention.

The device will ultimately decrease the frequency of dialysis whether it be peritoneal dialysis or hemodialysis for someone who is already on dialysis. In addition, the device might be used to provide supplemental function to delay the need for hemodialysis or peritoneal dialysis. Bottom line, it can be used in many phases of the patient's care.

The multiple wafer EDI unit of the invention may find uses in several applications where selective separations are important including food manufacturing, water treatment, other biomedical applications, etc. Furthermore, the unique EDI unit of the invention could be used for diseases other than just a global loss of transport, such as in chronic kidney disease or end stage kidney disease. Specifically, the technology could be used in patients with individual ion transport disorders where the individual (or in any combination) modulation of sodium, potassium, calcium, magnesium, phosphorus or bicarbonate excretion is required.

While the foregoing is directed to embodiments of the present invention, other and further embodiments of the invention may be devised without departing from the basic scope thereof, and the scope thereof is determined by the claims that follow.

Glossary permeate: in a pressure driven membrane separation system, that which passes through the openings or interstices of a liquid permeating membrane.

retentate: in a pressure driven membrane separation system, that which is retained, for example by a porous liquid permeating membrane.

dilute: in electrodeionization, the fluid on a first side of a separation membrane from which impurities are to be removed.

concentrate: In electrodeionization, the fluid stream on the second side of a separation membrane into which selected components are to be received. In a pressure driven membrane separation system, the fluid stream on one side of the separation membrane from which selected components are to be removed.

dilute stream: in electrodeionization one of the two fluid streams from which components (e.g. impurities) are to be removed, or have been removed.

concentrate stream: in electrodeionization, the other of the two fluid streams into which components (e.g. impurities) are to be received or have been received.

dialysate: (1) The fluid used on the other side of the membrane during dialysis to remove impurities. (2) The fluid and solutes in a dialysis process that flow through the dialyzer and do not pass through the semipermeable membrane, being discarded along with removed toxic substances after they flow back out of the dialyzer renal vein: a vein that drains the kidney renal artery: an artery that carries blood from the heart to a kidney.

CMX membrane: a membrane that allows for the transport (permeation) of positively charged ions there through, while rejecting the passage of negatively charged ions.

AMX membrane: a membrane that allows for the transport (permeation) of negatively charged ions there through, while rejecting the passage of positively charged ions.

BMX membrane: a membrane that rejects the passage there through of both positively and negatively charged ions.

What we claim is:

1. A wearable or implantable artificial kidney device comprising:
    an electrodeionization stack comprising:
        a first outer flow chamber on a first external boundary on a first side of the stack and next to a first exterior electrode, a second outer flow chamber on a second side of the stack and next to a second exterior electrode, wherein the inside wall of the first outer flow chamber and the inside wall of the and second outer flow chambers each comprise an ionic membrane disposed parallel to and spaced from the exterior electrodes,
        interior flow chambers comprising walls comprising a plurality of separation membranes, and wherein a plurality of the interior flow chambers are filled with resin having specific ion transport capabilities, and
        one or more electrodes associated with each of the interior flow chambers filled with resin; and
    one or more power supplies for selectively applying a voltage to one or more of the electrodes of the device.

2. The artificial kidney device of claim 1, wherein the one or more electrodes associated with each of the interior flow chambers filled with resin are disposed within the resin filled flow chambers.

3. The artificial kidney device of claim 1, wherein the one or more electrodes associated with each of the interior flow chambers filled with resin are each disposed on a side of a separation membrane.

4. The artificial kidney device of claim 1, where the one or more electrodes associated with each of the interior flow chambers filled with resin are porous.

5. The artificial kidney device of claim 4, wherein the one or more electrodes associated with each of the interior flow chambers filled with resin comprise wire mesh screens.

6. The artificial kidney device of claim 1, wherein the ionic membrane of the inside wall of the first outer flow chamber and the ionic membrane of the inside wall of the second flow chamber comprise a bipolar membrane.

7. The artificial kidney device of claim 6, wherein a first interior flow chamber adjacent the first outer flow chamber comprises a wall comprising an anion exchange membrane disposed parallel to and spaced from the first bipolar membrane, and wherein the first interior flow chamber is filled with a ion specific resin wafer.

8. The artificial kidney device of claim 7, comprising a second interior flow chamber comprising a first wall comprising the anion exchange membrane wall of the first interior chamber, and a second wall comprising a cation exchange membrane.

9. The artificial kidney device of claim 8, comprising a third interior flow chamber comprising a first wall comprising the cation exchange membrane of the second wall of the second interior flow chamber, and a second wall comprising the bi-polar exchange membrane of the interior wall of the second outer flow chamber, wherein the third interior flow chamber is filled with a ion specific resin.

10. The artificial kidney device of claim 9, wherein the ion specific resin wafer of the third interior flow chamber is specific for a different ion that the ion specific resin wafer of the first interior flow chamber.

11. The artificial kidney device of claim 1, wherein the ionic membrane of the inside wall of the first outer flow chamber and the ionic membrane of the inside wall of the second flow chamber comprise a cation exchange membrane or an anion exchange membrane.

12. The artificial kidney device of claim 1, wherein the resin is presented in a form of pressed sheets of immobilized resin wafers.

13. The artificial kidney device of claim 1, wherein positioned between each of the plurality of interior flow chambers filled with resin is a resin-free fluid flow chamber.

14. The artificial kidney device of claim 1, comprising three resin filled flow chambers, wherein each resin filled flow chamber having associated with it a separate resin-free fluid flow chamber, and each resin filled flow chamber is filled with a different ion specific resin.

15. The artificial kidney device of claim 1, comprising an ultrafiltration pretreatment membrane.

16. The artificial kidney device of claim 1, comprising a nanofiltration membrane for selective separation of glucose from urea.

17. The artificial kidney device of claim 1, comprising a reverse osmosis membrane for water management.

18. The artificial kidney device of claim 1, comprising a ultrafiltration membrane, a nanofiltration membrane, and a reverse osmosis membrane.

19. The artificial kidney device of claim 1, wherein alternating interior flow chambers are filled with resin.

20. The artificial kidney device of claim 1, wherein the plurality of interior flow chambers that are filled with resin are filled with resin wafers.

* * * * *